United States Patent [19]

Kussick

[11] Patent Number: 5,885,073
[45] Date of Patent: Mar. 23, 1999

[54] ORTHOPEDIC INCLINE APPLIANCE AND METHOD

[75] Inventor: Leon Kussick, Livingston, N.J.

[73] Assignee: Kussick Orthodontic Systems, LLC, Naples, Fla.

[21] Appl. No.: 660,442

[22] Filed: Jun. 7, 1996

Related U.S. Application Data

[60] Provisional application No. 60/000,098 Jun. 9, 1995.
[51] Int. Cl.⁶ .................................................... A61C 7/00
[52] U.S. Cl. ............................................... 433/6; 128/848
[58] Field of Search ....................... 433/6, 140; 128/848, 128/861, 862; 600/237, 238

[56] References Cited

U.S. PATENT DOCUMENTS

| | | | |
|---|---|---|---|
| 2,567,810 | 9/1951 | Harper | 433/72 |
| 3,016,052 | 1/1962 | Zubren | 128/862 |
| 3,207,153 | 9/1965 | Goldstein | 128/862 |
| 3,219,033 | 11/1965 | Wallshein . | |
| 3,277,892 | 10/1966 | Tepper . | |
| 3,286,576 | 11/1966 | West | 84/466 |
| 3,312,216 | 4/1967 | Wallshein . | |
| 3,334,417 | 8/1967 | Spengeman | 128/862 |
| 3,478,742 | 11/1969 | Bohlmann . | |
| 3,510,946 | 5/1970 | Kesling | 32/14 |
| 3,522,805 | 8/1970 | Wallshein . | |
| 3,871,370 | 3/1975 | McDonald | 128/136 |
| 3,884,226 | 5/1975 | Tepper . | |
| 3,898,736 | 8/1975 | Bergersen . | |
| 3,939,598 | 2/1976 | Bergersen . | |
| 4,169,473 | 10/1979 | Samelson . | |
| 4,185,817 | 1/1980 | Peterson | 272/95 |
| 4,304,227 | 12/1981 | Samelson . | |
| 4,337,036 | 6/1982 | Hoffman | 433/5 |
| 4,504,225 | 3/1985 | Yoshii | 433/6 |
| 4,553,549 | 11/1985 | Pope et al. . | |
| 4,569,342 | 2/1986 | von Nostitz | 128/862 |
| 4,608,974 | 9/1986 | Sicurelli, Jr. . | |
| 4,671,766 | 6/1987 | Norton | 433/6 |
| 4,718,662 | 1/1988 | North | 272/95 |
| 4,773,853 | 9/1988 | Kussick | 433/6 |
| 4,986,283 | 1/1991 | Tepper | 128/859 |

(List continued on next page.)

FOREIGN PATENT DOCUMENTS

| | | |
|---|---|---|
| 0264516 | 4/1988 | European Pat. Off. ............... 128/848 |
| WO 92/05752 | 4/1992 | European Pat. Off. . |

OTHER PUBLICATIONS

Dr. Leon Kussick, Bone Remodeling Orthodontics: An Early, One–Phase, Non–Extraction Therapy—Part II, *The Functional Orthodontist*, vol. 12, No. 1, pp. 4–15 (1995).

Dr. Leon Kussick, Bone Remodeling: The Next Generation of Orthodontics a Total, Early Non–Extraction Approach, *The Functional Orthodontist*, Mar./Apr. pp. 1–8 (1985).

E. A. Mitchell et al., Dummies and the Sudden Infant Death Syndrome, *Archives of Disease in Childhood*, 68:501–504 (1993).

James Woodford, How Sucking On Dummies May Save Your Baby's Life, Appeared in (Australia) *Sidney Morning Herald*, Aug. 19, 1993.

Snoring/Sleep Apnea Adjustable Appliance, Dental Products Report, p. 89, Jun. 1996.

*Primary Examiner*—Ralph A. Lewis
*Attorney, Agent, or Firm*—Dechert Price & Rhoads

[57] ABSTRACT

The invention provides to a prefabricated appliance for correcting many types of malocclusions typically with no more than limited use of wires or bands. The appliance is designed to be fitted stably and tightly to the upper front teeth or back teeth when needed. The appliance comprises: a teeth engaging box adapted to engage the upper front teeth; a stabilizing segment attached to the teeth engaging box and adapted to permit a stable and comfortable fitting of the appliance in a patient's mouth; and a pair of spaced inclined remodeling segments extending from in front of the teeth engaging box downward and rearward at a predetermined angle designed so that the inclined remodeling segments contact the lingual contacting surface of selected lower front teeth and urge the lower jaw forward and upward to the desired degree.

14 Claims, 5 Drawing Sheets

U.S. PATENT DOCUMENTS

| | | | |
|---|---|---|---|
| 4,986,751 | 1/1991 | Bergersen | 433/6 |
| 5,003,994 | 4/1991 | Cook | 128/848 |
| 5,018,533 | 5/1991 | Hawkins . | |
| 5,052,409 | 10/1991 | Tepper | 128/859 |
| 5,056,534 | 10/1991 | Wright | 433/140 |
| 5,092,346 | 3/1992 | Hays et al. . | |
| 5,133,740 | 7/1992 | Kussick | 606/236 |
| 5,277,202 | 1/1994 | Hays | 128/862 |
| 5,316,020 | 5/1994 | Truffer | 128/848 |
| 5,406,963 | 4/1995 | Adell | 128/862 |

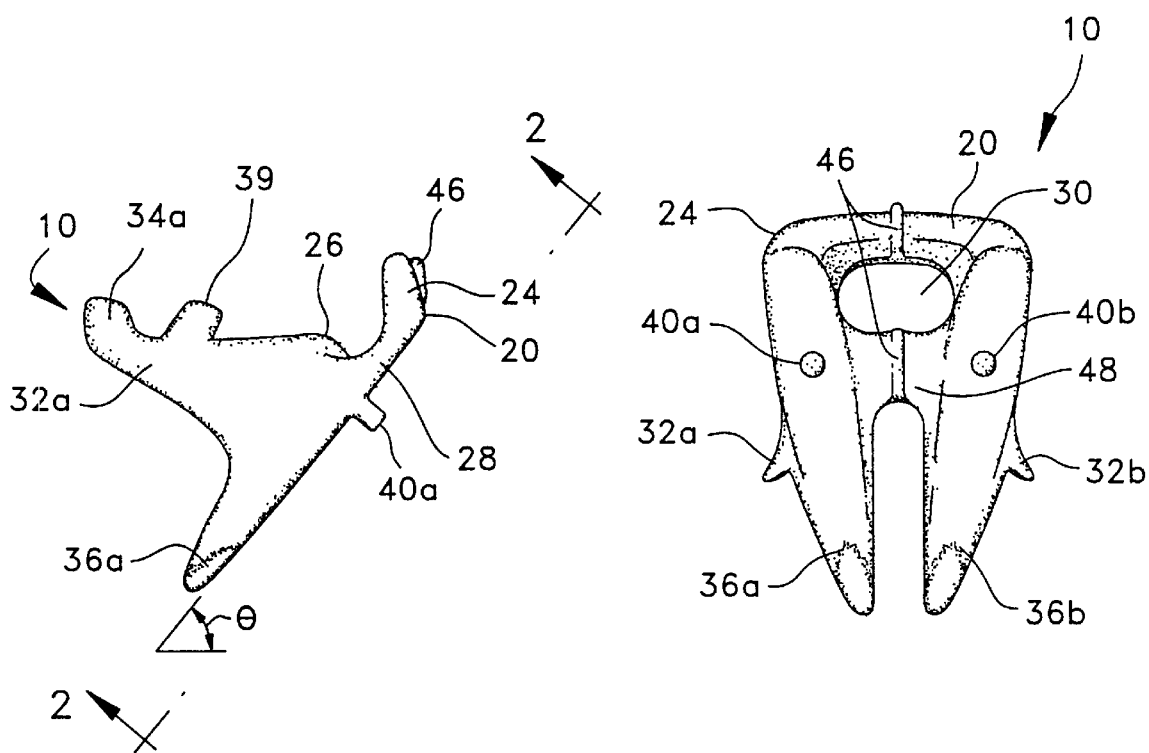
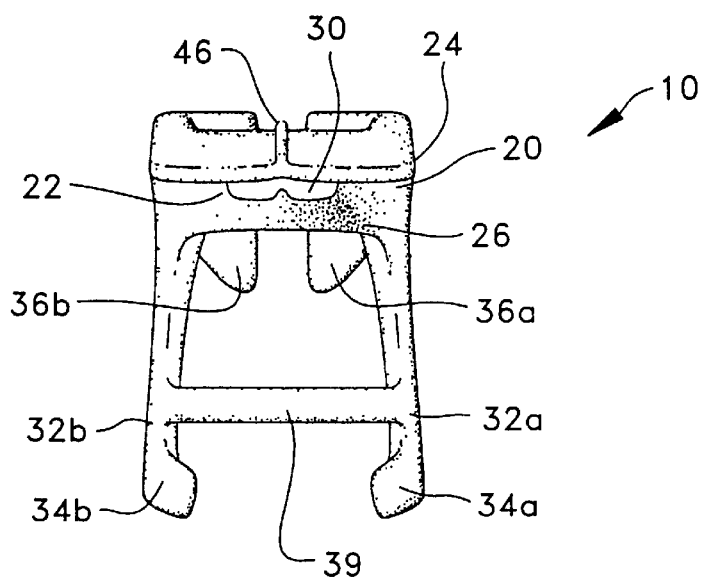
FIG. 1
FIG. 2
FIG. 3

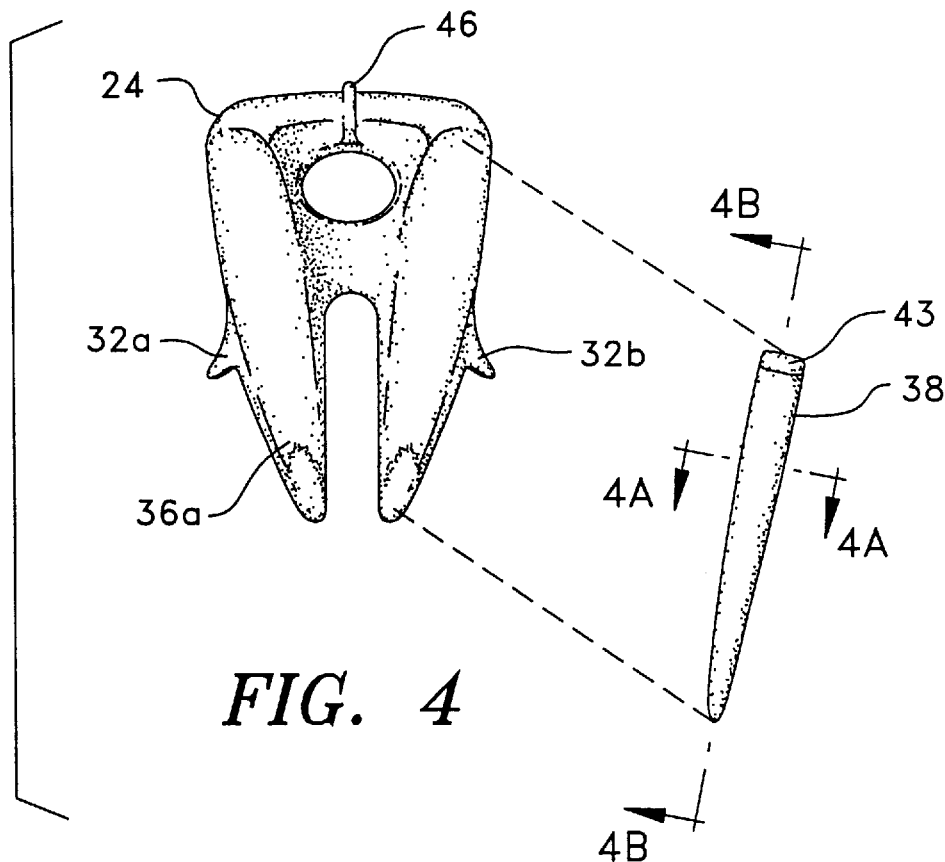
FIG. 4
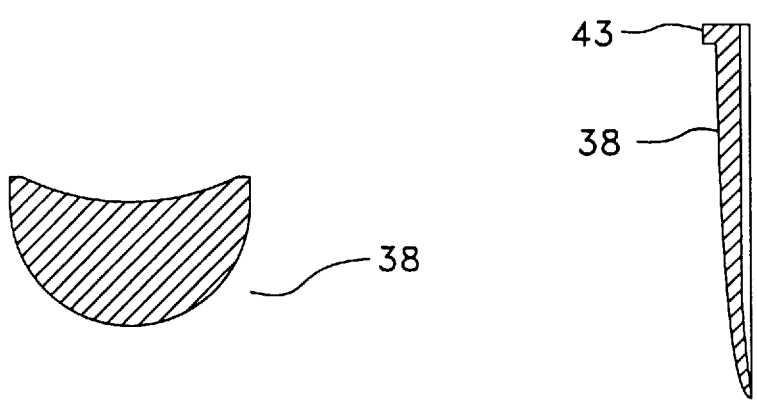
FIG. 4A          FIG. 4B

ORTHOPEDIC INCLINE APPLIANCE AND METHOD

This application claims benefit of Provisional application 60/000,098 filed Jun. 9, 1995.

The present invention is directed to a prefabricated appliance for correcting malocclusions, i.e., abnormalities in the jaw or teeth alignment.

The applicant has previously described an appliance for correcting malocclusions (i.e., jaw and occlusal or tooth irregularities) in U.S. Pat. No. 4,773,853. The applicant has found this appliance to be effective in correcting malocclusions. The appliance of U.S. Pat. No. 4,773,853, however, is difficult to stabilize and it is difficult to accurately position the inclined remodeling segments of the appliance in a patient's mouth absent sufficient experience. Furthermore, in some cases, it has been difficult to obtain a strong bond between the preformed appliance and the polymer which is added to achieve a proper, tight fit to a patient's upper front teeth. Also, the appliance can be difficult to center and align in certain situations, and adjusting the angle of the inclined remodeling segments that mediate the corrective effects of the device can be difficult. Accordingly, features have been added to the basic device of U.S. Pat. No. 4,773,853 to permit a easier, more stable and firm fitting in a patient's mouth, to encourage a stronger bond between the preformed appliance and the added polymer, and to facilitate proper centered alignment without lateral or horizontal tipping of the appliance during the fitting procedure. The better fit achieved with the improved device limits the unwanted movement of the device and thereby limits irritation to soft tissue that would result if the device shifted during use and, as a result, contacted soft tissue. The improved design is also mechanically stronger. The entire disclosure of U.S. Pat. No. 4,773,853 (the '853 patent) is incorporated herein by reference.

The appliance of the '853 patent has a teeth engaging box for tightly fitting, in conjunction with a polymerizable material, the appliance to the upper front teeth of the patient, a pair of winged segments extending posteriorly, and a pair of inclined remodeling segments adapted to contact the lower lateral incisal edges to position the patient's lower jaw forward and/or upward relative to the upper jaw. The re-positioning of the lower jaw develops tension on the jaw's muscle attachments. While not wishing to be limited by theory, it is believed that such tension initiates jaw relocation, and that the appliance functions clinically by directing appropriate muscle attachment stimuli to initiate the bone growth mechanism of the jaws.

SUMMARY OF THE INVENTION

In one embodiment, the invention relates to an appliance for correcting malocclusions that has a bilateral stabilizing contact with the palate. This contact simplifies the fitting process, fixes the incline of the inclined remodeling inclined segments, and allows less experienced orthodontists, dentists or technicians to properly and quickly fit the appliance to any patient. The appliance comprises: a) a teeth engaging box for engaging the upper front teeth having a cavity into which the engaged teeth fit; b) a palatal stabilizing segment attached to the teeth engaging box and adapted to bilaterally contact the palate when the teeth engaging box engages the upper front teeth; and c) a pair of forward positioned spaced inclined remodeling segments extending from in front of the teeth engaging box downward and rearward at a predetermined angle.

Preferably, the palatal stabilizing segment comprises a pair of palatal extending portions each having a palate contact pad at their rearward end adapted to contact the palate, wherein the combination of the two palate contact pads and the teeth engaging box allows a routine stable positioning of the appliance and the palatal extending portions extend parallel to the surface of the palate.

This embodiment allows the appliance to be stably positioned in a patient's mouth while the appliance is being fitted by simultaneously contacting the palate and upper incisal edges of the front teeth. The stability of the positioning during the initial fitting prior to the application of the polymerizable material that molds the appliance to the shape of the front teeth allows either (a) for the selection of a device with an appropriate angle of the inclined remodeling segments or (b) for the adjustment of the angle by, for instance, sculpting or selecting and joining appropriate incline addition segments. The inclined remodeled segments can be sculpted by removing material, typically by grinding, or adding material using for example, a polymerizable material. The angle of the inclined remodeling segments should preferably be adjusted so that each contacts smoothly the incisal edges of the lower lateral incisors. Of course, in a particular treatment, the alignment of the patient's teeth may require adjustments in this approach. After the appliance is fitted to the patient's upper front teeth, the portion of the appliance that is adapted to contact and rest against the palate is preferably sculpted away before regular clinical use of the appliance to permit a more comfortable wearing of the appliance, and to avoid palatal soft tissue irritation.

The invention further provides a first dental kit comprising an appliance of the invention and sufficient polymerizable material to fit the appliance to a patient's mouth. Preferably, where the polymerizable material is polymerizable by light curing, the first kit further comprising a means or package for protecting the polymerizable material from light.

The invention further provides a method of fitting the appliance of the present invention to a patient comprising the steps of: 1) fitting the polymerizable material into the cavity of the teeth engaging box; 2) molding the polymerizable material to the shape of the patient's upper front teeth while visually aligning the center of the appliance with the centerline of the patient's teeth or mouth and stabilizing the seating of the appliance in the patient's mouth by contacting the stabilizing segment with the palate; 3) removing the appliance from the molded teeth; and 4) fully curing the polymerizable material to increase its strength. The method can further comprise the step of initially and partially curing the polymerizable material following molding step and before the removing step. The molding step comprises impressing the upper front teeth into the polymerizable material until the incisal edges of the teeth contact the bottom of the teeth engaging box cavity. The molding should preferably mold the polymerizable material so the it engulfs the crowns of the engaged teeth. Where the appliance has a hole such as bevelled hole, the molding step further comprises molding the polymerizable material so that polymerizable material is molded to both sides of the hole. Furthermore, the method can comprise, after the curing, the step of removing the palate-contacting portion of the palatal stabilizing segment so that it will no longer rest against the palate when the appliance is seated in the patient's mouth. The use of the palatal stabilizing segment during the fitting helps assure that the inclined remodeling segments of the fitted appliance shall have the proper angle of incline and helps align the appliance with the center of the mouth.

The invention further provides a second dental kit comprising: d) an orthodontic appliance comprising a teeth engaging box for engaging the upper front teeth having a cavity into which the engaged teeth fit; a palatal stabilizing segment attached to the teeth engaging box; and a pair of forward positioned spaced inclined remodeling segments extending from in front of the teeth engaging box downward and rearward at a predetermined angle; e) at least one addition segment adapted to be joined to one inclined remodeling segment to, in conjunction with the inclined remodeling segment, create a new inclined remodeling surface with an altered angle or to move the inclined remodeling segment further forward relative to the teeth engaging box; and f) sufficient polymerizable material to join the addition segment to the inclined remodeling segment. Preferably, the addition segment comprises a stop for establishing the position of a patient's teeth against the remodeling surface, wherein the location of the stop can be adjusted by adjusting the position at which the addition segment is joined to the inclined remodeling segment.

The invention further provides an appliance for correcting malocclusions comprising: g) a teeth engaging box for engaging the upper front teeth having a cavity into which the engaged teeth fit, wherein the teeth engaging box comprises a trench for engaging the front teeth comprising (1) a front molding elevation joined to (2) a connector joined to (3) a rear molding elevation, wherein the front molding elevation and rear molding elevation and connector of the teeth engaging box form one or more holes in the teeth engaging box; h) a palatal extending segment attached to the teeth engaging box; and i) a pair of spaced inclined remodeling segments extending from in front of the teeth engaging box downward and rearward at a predetermined angle.

The invention further provides an appliance for correcting malocclusions comprising: j) a teeth engaging box for engaging the upper front teeth having a cavity into which the engaged teeth fit; k) a palatal extending segment attached to the teeth engaging box; l) a pair of spaced inclined remodeling segments extending from in front of the teeth engaging box downward and rearward at a predetermined angle; and m) a means for visually aligning the center of the appliance. Preferably, the means for aligning the center of the appliance is situated on the front molding elevation of the teeth engaging box. Preferably, the teeth engaging box comprises a trench for engaging the front teeth comprising (1) a front molding elevation joined to (2) a connector joined to (3) a rear molding elevation, wherein the front and rear molding elevation and connector of the teeth engaging box form one or more holes in the teeth engaging box located over the tips of the front teeth.

The invention still further provides an appliance for correcting malocclusions comprising: n) a teeth engaging box for engaging the upper front teeth having a cavity into which the engaged teeth fit; o) a pair of palatal extending portions, wherein the extending portions are adapted to extend parallel to the surface of the palate; p) a palatal bridge joining the two palatal extending portions, wherein the palatal bridge is adapted to parallel the surface of the palate; and q) a pair of forward positioned spaced inclined remodeling segments extending from in front of the teeth engaging box downward and rearward at a predetermined angle.

The invention further provides an appliance for correcting malocclusions comprising: r) a teeth engaging box for engaging the upper front teeth having a cavity into which the engaged teeth fit; s) a pair of occlusal troughs adapted to fit under at least one, on each side, of the upper posterior teeth; and t) a pair of forward positioned spaced inclined remodeling segments attached to the front of the planar segment and extending downward and rearward at a predetermined angle. In this embodiment, the inclined remodeling segments are situated in the patient's mouth in the same way they are in the above-described embodiments. The appliance is fitted to the patient using the rear teeth on both sides in addition to the front teeth—though preferably in this embodiment the front teeth are engaged through a teeth engaging segment. A polymerizable material is (1) applied to the upper surface of the occlusal troughs, (2) molded to conform to the shape of the rear teeth located under the occlusal troughs, and (3) cured to increase its strength. In a preferred embodiment, attached to each occlusal trough are one or more side exterior molding walls or elevations adapted to fit in the patient's mouth in front of or behind at least about two of the teeth under which the occlusal trough fits. In another preferred embodiment, the occlusal troughs have at least one hole each suitable for engaging a polymerizable material to facilitate bonding between the device and the polymerizable material.

In all embodiments of the appliance, preferably, the palatal stabilizing segment of the appliance comprises two palatal extending portions connected by a palatal bridge. Preferably, the teeth engaging box comprises a trench for engaging the upper front teeth comprising (1) a front molding elevation having a front and rear surface joined to (2) a connector joined to (3) a rear molding elevation having a front and rear surface, wherein: i.) the rear surface of the front molding elevation is adapted to seat in front of at least one front tooth when the appliance is fitted to the patient; and ii.) the front surface of the rear molding elevation is adapted to fit behind at least one front tooth when the appliance is fitted to the patient. Preferably the front and rear molding elevations and connector of the teeth engaging box form one or more holes in the teeth engaging box located in front of the front teeth. Preferably, the one or more holes, either in the teeth engaging box or the occlusal troughs, have bevelled edges suitable for engaging polymerizable material to facilitate bonding between the appliance and the polymerizable material. Preferably, the holes have angled or bevelled edges to allow portions of the polymerizable material having greater diameter than the hole to be molded on both sides of the hole. These larger diameter portions act as plugs or undercuts that stabilize the polymerizable material from separating from the preformed device. Preferably, the appliance further comprises a means for visually aligning the center of the appliance that can be situated on the front molding elevation of the teeth engaging box or on a connector piece connecting the two inclined remodeling segments.

It will be recognized that a number of preferred embodiments that are specifically described with reference to a particular embodiment of the appliance for correcting malocclusions are equally applicable to other embodiments.

The invention further provides a palatal depth measuring device comprising: u) a horizontal platform of the suitable dimensions to seat on the upper posterior teeth, on both sides of a patient's mouth; v) a vertical depth measuring rod; and w) a means for vertically, movably engaging the rod with the platform, the means adapted to align the rod with the center line of a patient's mouth.

In adults the bone growth mechanisms that can be used to correct malocclusions in juveniles often no longer function, and in adults the appliance is of limited orthodontic use. However, the appliance can be worn at night by adults to bring the lower jaw comfortably forward to keep open the nasopharynx space to thereby help reduce snoring or the noise level of a user's snoring by increasing unobstructed air flow. Accordingly, the invention also relates to a method of attenuating snoring by wearing during sleep an appliance comprising: 1) a teeth engaging box for engaging the upper front teeth having a cavity into which the engaged teeth fit; and 2) a pair of forward positioned spaced inclined remodeling segments extending downward and rearward from the teeth engaging box at a predetermined angle, preferably matching the angle of the rear surface of the lower lateral incisors. Of course, preferred features of the appliance recited above which help to fit the appliance to the patient can be used in the snoring reduction method. Particularly preferred are the occlusal troughs that fit the device to teeth located in the rear of the mouth.

BRIEF DESCRIPTION OF THE DRAWINGS

FIG. 1 displays a side view of the of an embodiment of the inventive appliance.

FIG. 2 displays a front view of an embodiment of the inventive appliance.

FIG. 3 displays a top view of an embodiment of the inventive appliance.

FIG. 4 displays a front view of an embodiment of the appliance along with an addition segment designed to be added to the inclined remodeling segment of the appliance as indicated.

DEFINITIONS

* incline addition segment

Figure 5:
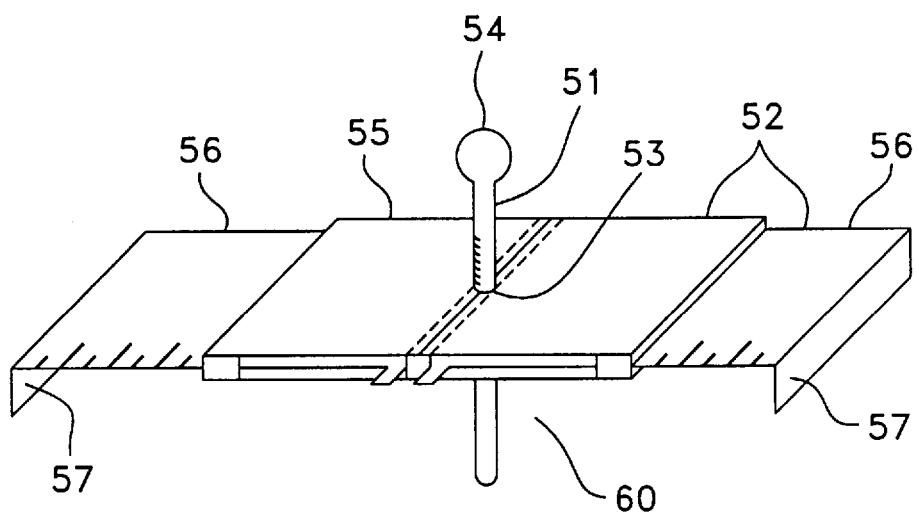
FIG. 5 displays a measurement device of the invention.
Figure 6:
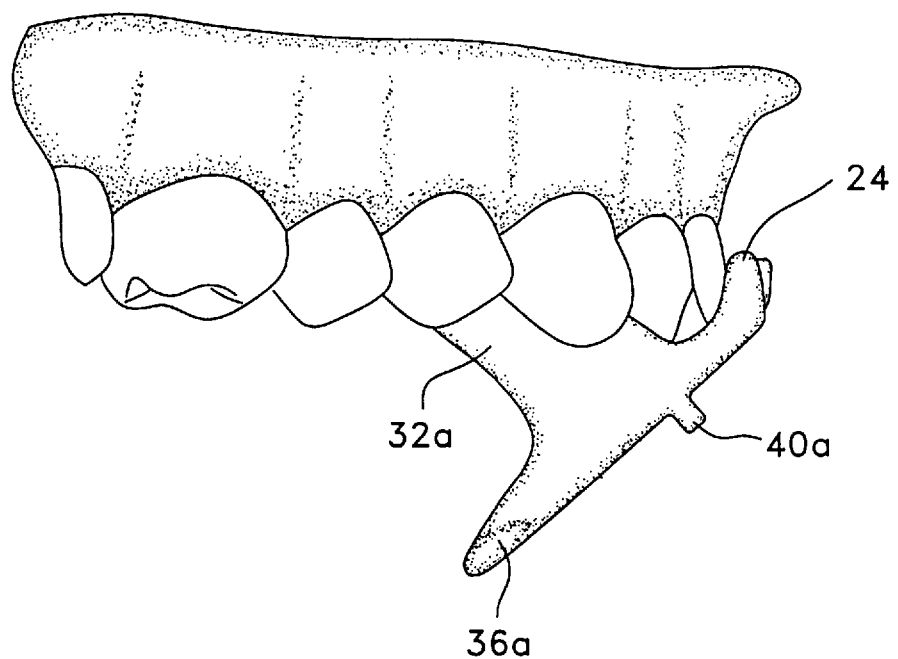
FIG. 6 display views of an embodiment of the inventive appliance.

An incline addition segment is a piece that is designed to be fitted to the front of an inclined remodeling segment to adjust the angle of incline, the amount that the inclined remodeling segment projects forward, or the position of a ledge, stop or barrier that serves to restrict the positioning of the lower front teeth that contact the inclined remodeling segment.

* inclined remodeling segment

The appliance of the invention typically has two inclined remodeling segments. The inclined remodeling segments are each designed to evenly contact the incisal edges of a lower incisor of a patient, with each inclined remodeling segment typically engaging a lower lateral incisor. The amount that the inclined remodeling segments are positioned forward (to thereby move the jaw horizontally forward) and the amount that the engaged teeth are allowed to move up the incline of the inclined remodeling segments (to thereby vertically adjust jaw location) determines the amount of tension placed on the musculature of the jaw, thereby, it is believed, adjusting the stimulus to the bone growth mechanism.

* inclined remodeling surface

The appliance is designed to contact lower front teeth either directly through the front surfaces of the inclined remodeling segments or through attached incline addition segments; in either case, the surface intended to contact the lower front teeth is the "inclined remodeling surface."

* molding walls or elevations

An exterior molding wall or elevation is an elevation on either side of a trough designed to support the polymerizable material that will be molded to the shape of some of a patient's upper back teeth. The elevations serve to support and facilitate shaping the polymerizable material to conform to the outer surfaces of the teeth.

* occlusal trough

A trough segment is a piece designed to facilitate molding of an appliance of the invention to the occlusal and side surfaces of the molars.

* palatal extending portion

A palatal extender portion is one of two such palatal extending portions that extend rearward, and slightly upwards, from the teeth engaging box and serve (a) to provide supports for palate contact pads and (b) to sufficiently expand the cross-sectional area of the appliance so that it cannot be swallowed.

* polymerizable material

A polymerizable material is any material that can be molded to conform to the shape of one or more teeth and subsequently cured to lock it into the molded shape.

* posterior teeth

The posterior teeth are the teeth behind the canines; these teeth are sometimes called the buccal or cheek teeth.

* stabilizing segment

A structure attached to the appliance of the invention that serves to provide a broad, preferably two point, contact with the palate to stabilize the appliance during fitting to a patient. Preferably, the points of contact with the palate are sufficiently broad and smooth such that contact irritation to the patient is minimized.

* substantially parallel

Palatal extending portions or a bridge linking two palatal extending portions are preferably substantially parallel to the palate, meaning that their upper surface is adapted to sit from about 1 mm to about 3 mm from the palate.

* teeth engaging box

The teeth engaging box is a segment of the appliance of the invention that is designed to provide a framework for molding the polymerizable material used to fit appliance to the patient's upper front teeth.

DETAILED DESCRIPTION OF THE INVENTION

The inventive appliance denoted as 10 in FIGS. 1, 2, 3 and 4 is molded of a polymer such as polycarbonate or other polymeric material such as an approved biocompatible polymer to fit a wide range of mouths. Appliance 10 includes a teeth engaging box 20 having a cavity 22 (visible in FIG. 3) for engaging the upper front teeth. (All directional references in the description of the appliance, e.g. "above" or "front", refer to the appliance as it would sit in a patient's mouth.) In a preferred embodiment of appliance 10 displayed in FIGS. 1, 2, 3 and 4, teeth engaging box 20 is formed of a front molding elevation 24 and a rear molding elevation 26 joined by a connector 28. The rear surface of front molding elevation 24 and the front surface of rear molding elevation 26 can be adapted to seat in front of and behind, respectively, at least one front tooth when appliance 10 is fitted to a patient. The front molding elevation can be slightly rearwardly curved. Preferably, these molding elevations are adapted to seat adjacent to the upper front two teeth, i.e., the central incisors. When the patient lacks one of these central teeth or one is still erupting, one or more other front teeth can be substituted for the missing tooth. Front molding elevation typically extends about 4 to about 8 mm above the floor of the teeth engaging box 20 against which the tips of the engaged front teeth seat. Rear molding elevation typically extends about 2 to about 3 mm above the floor of the teeth engaging box 20 against which the tips of the engaged front teeth seat. Preferably, the front molding elevation 24 and rear molding elevation 26 define a trench into which the front teeth fit that is from about 5 mm to about 10 mm in width. The lateral molding elevations, namely front molding elevation 24 and rear molding elevation 26, serve to support and contain the polymerizable material when it is inserted into the teeth engaging box 20 to mold the appliance 10 to the shape of the patient's teeth.

In the preferred embodiment of appliance 10 displayed in FIGS. 2, 3 and 4, a hole 30 is formed in front molding elevation 24, rear molding elevation 26 and connector 28 of teeth engaging box 20 whereby the hole 30 is located in front of the upper front, central two teeth and the incisal edges or lowest portions (referred to herein as the "tips") of these two teeth. Rather than contain a single hole 30, the teeth engaging box 20 could contain two or more holes. Preferably, hole 30 has angled or bevelled edges to allow portions of the polymerizable material used to fit appliance 10 (as described more fully below) and having greater diameter than hole 30 to be molded on both sides of hole 30. These larger diameter portions act as plugs or undercuts that stabilize the cured polymer from separating from the preformed appliance 10. This bonding stabilization is particularly relevant during the process of molding polymerizable material to conform to the shape of a patient's teeth, at which point the bond between the appliance and the uncured or partially cured polymerizable material is generally weaker than it will be after further curing.

Attached to teeth engaging box 20 are a pair of upwardly and rearwardly extending palatal portions 32, termed the first palatal portion 32a and second palatal portion 32b, which extend parallel to but relieved from the palate. The palatal portions 32 are preferably shaped to minimize their interference with the movement of the patient's tongue. In a preferred embodiment of appliance 10 displayed in FIGS. 1 and 3, each of the first extending portion 32a and second extending portion 32b has at its rearward end a palatal contact pad 34, the two termed the first palate contact pad 34a and second palate contact pad 34b; and the first palate contact pad 34a and second palate contact pad 34b are adapted to provide a platform to bilaterally support the appliance 10 during fitting. The first palatal extending portion 32a and second palatal extending portion 32b and first palate contact pad 34a and second palate contact pad 34b are a "stabilizing" segment, as defined above. The combination of the teeth engaging box 20 and the palate contact pads 34 allow for correct and stable positioning of appliance 10, which, as discussed above, facilitates centering the appliance 10 and adjusting the angle of the inclined remodeling segments 36. In a preferred embodiment of appliance 10, extending portions 32 are of sufficient dimensions to prevent accidental swallowing of appliance 10. Thus, palatal extending portions 32 generally are at least about 2.5 cm in length (measured along the central axis from the rearward part of a given extending portion to the intersecting plane of the front of the inclined remodeling segments), and palate contact pads 34 generally are centered at least about 1.5 cm apart. The palatal extending portions 32 are generally from about 2.5 to about 4.5 cm in length, preferably about 3.0 to about 4.0 cm in length. Preferably the palatal extending portion 32 (less the palatal contact pads 34) is adapted to parallel the palate while separated therefrom by about 2 mm.

Preferably, the two palatal extending portions 32 are linked together by a palatal bridge 39, preferably upwardly curving, that substantially parallels the palate. The bridge 39 serves to strengthen the appliance 10. Preferably, the palatal bridge 39 is located at a rearward position such as a position at least about 60% of the length of the palatal extending portions to the rear.

A pair of spaced inclined remodeling segments 36, termed first inclined remodeling segment 36a and second inclined remodeling segment 36b, extend from in front of teeth engaging box 20 downward and rearward at a predetermined angle relative to the posterior occlusal plane. This angle, θ, will generally be between about 40 and about 45 degrees. This angle has been found to promote the movement of the engaged lower front teeth up the inclined remodeling surface to the stop 40. In some patient's the architecure of the lingual anterior region of the lower jaw will dictate the final angle, for instance requiring an angle of about 35 to about 45 degrees. The shape of the inclined remodeling surface should be adapted to promote the movement of the engaged lower teeth up the inclined remodeling surface to the stop 40. In certain instances the angle referred to above will have to be individually adjusted over time for the original malocclusion and over time as the malocclusion begins to change and correct. Thus, initially, first inclined remodeling segment 36a and second inclined remodeling segment 36b can have varying incline angles as part of an initial strategy to relocate the lower jaws more vertically rather than horizontally or to prevent contact with soft tissue located behind the roots of the lower front teeth. As the positioning of the lower jaw is corrected by the effect of muscle tension caused by the continued use of appliance 10 (resulting in the lower jaw moving forward or downward), reshaping or replacement of the first inclined remodeling segment 36a and second inclined remodeling segment 36b may be required. Alternatively, it may be desirable to maintain the same angle, but to move the incline of the inclined remodeling segments forward in the mouth of the patient or to make the inclined remodeling segments longer in either their top or bottom portion. The inclined remodeling segments are generally adapted to engage the lower lateral front teeth (specifically, the lateral incisal edges). Although engaging the lateral incisors is most preferred, in a particular case it may be necessary to engage teeth other than these lower lateral incisors. This engagement increases jaw muscle tension, which helps relocate the lower jaw downwards or forward. The engagement also moves the engaged teeth forward and develops more arch room in the alveolus bone, which aids the alignment of the lower front teeth. Generally, the inclined remodeling segments will be spaced from about 5 to about 8 mm apart at their lower ends.

As mentioned above, the angle of the inclined remodeling segments should preferably be adjusted so that each contacts smoothly the incisal edges of the lower lateral incisors. Of course, in a particular treatment, the alignment of the patient's teeth may require adjustments in this approach. For instance, if one lower lateral incisor is positioned well behind the other, it may not be practical to engage both such incisors; instead the furthest rearwardly positioned such incisor will be initially engaged. In some patients, one such incisal edge may be so crookedly oriented that only a corner of the tooth can initially be engaged, instead of a broader part of the incisal edge being smoothly engaged.

Generally, the two inclined remodeling segments tend to move farther apart when going from their lower ends to their upper ends. This divergence helps avoid contacting the incisors after the lower teeth slide up the incline to the stop and helps avoid soft tissue contact. Note that the bottom portions of first inclined remodeling segment 36a and second inclined remodeling segment 36b are bevelled to angle more rearwardly and more inwardly. This bevelling is indicated in the drawings with shading. Bevelling helps avoid contact with sub-lingual soft tissue.

For additional post-initial fitting adjustments of the appliance, an incline addition segment 38 (displayed in FIG. 4) may be joined to each of first inclined remodeling segment 36a and second inclined remodeling segment 36b using a polymerizable material, such as the polymerizable material used to fit appliance 10 to a patient's mouth. The addition segment 38 can be used to bring the inclined remodeling surface further up, down or forward, so that they will guide the lower jaw to adjust the tension on the muscle attachments of the lower jaw. The addition segments 38 can also be used to adjust the angle of the inclined remodeling surface.

First stop 40a (visible in FIG. 1) and second stop 40b, located on first inclined remodeling segment 36a and second inclined remodeling segment 36b, respectively, provide barriers or ledges to restrict the lower jaw's upward movement along the inclined remodeling segments 36 of the lower front teeth engaged by the inclined remodeling segments. Collectively, these are "stops" 40 (not shown). Stops 40 can be placed on the appliance 10 at locations found to be generally useful, or can be added later, generally by molding such stops 40 from a polymerizable material. Pre-formed stops 40 at locations not useful to a particular treatment or no longer useful to a treatment can easily be ground down. The appliance will preferably have at least one such pre-formed stop 40 per inclined remodeling segment. Incline addition segment 38 has a pre-formed stop 43. Such incline addition segments can be made with pre-formed stops at other positions. However, preferably, the location of the stop 43 will be adjusted merely by adjusting the location at which the addition segment 38 is joined to the appliance 10. Depending on the type of malocclusion to be corrected, the stop 43 or stop 40 will be located higher or lower on first inclined remodeling segment 36a, second inclined remodeling segment 36b or addition segment 38.

Stops 40 located lower on the inclined remodeling segments 36 are useful for treating primarily deep bites. Stops 40 located at intermediate positions on the inclined remodeling segments 36 are useful for treating deep bits and moderate overjets. Stops 40 located higher on the inclined remodeling segments 36 are useful for treating more severe overjets.

In the preferred embodiment of appliance 10 displayed in FIGS. 1, 2 and 3, a centrally located midline ridge 46 situated on the front molding elevation 24 as well as on connecting piece 48, which connecting piece 48 is symmetrically attached to first inclined remodeling segment 36a and second inclined remodeling segment 36b, serves as a means for aligning appliance 10 in a patient's mouth. Other means, such as notches, marks, lines, creases, knobs or colored lines (including painted lines located along the midline of appliance 10) could also serve to align appliance 10. To align appliance 10, ridge 46 or similar alignment means is visually aligned with a centrally located feature of the patient's face, such as the nose or, if not offset by a malocclusion, the center between the upper two front teeth.

The appliance 10 is fitted to a patient's front teeth or to a work model made from an impression of the patient's upper teeth and mouth using a curable material (referred to herein as "polymerizable") which preferably is light curable, although other means of curing, such as for example heat curing, chemical curing and pressure curing, may be used. Prior to curing, this material should have a workable tack so that it can be manipulated yet will, at least for the short term, maintain a formed shape. A preferred polymerizable material is a urethanedimethacrylate material such as TRIAD VLC Provisional material (rope form) from Densply of York, Pa. The polymerizable material is applied to cavity 22 of teeth engaging box 20. When TRIAD rope is used, preferably the appliance is wetted with a monomer solution such as the urethane-dimethacrylate monomer of the gel form of TRIAD VLC (Densply) or methyl methacrylate monomer (such as the solution sold as Orthodontic Resin, by the L. D. Cork division of Densply, Milford, Del., TRIAD VLC Bonding Agent from Densply, or SNAP liquid monomer from Parkell, Farmingdale, N.Y.) prior to applying the TRIAD rope material. Wetting with TRIAD VLC Bonding Agent can be conducted as recommended by the manufacturer, which recommended process includes (a) applying the Bonding Agent, (b) allowing the applied Bonding Agent to sit for one minute, and (c) exposing the applied Bonding Agent to a suitable light source for two minutes. The recommended process is believed to minimize the amount of methylmethacrylate monomer present. Preferably, the attachment of the polymerizable material to the appliance 10 will be further anchored by being plugged into hole 30. Appliance 10 is then centered and fitted to the upper front teeth, or the model thereof, while aligning the center of appliance 10 with the centerline of the patient's mouth and also stabilizing the seating of appliance 10 in the patient's mouth by bilaterally contacting both first palate contact pad 34a and second palate contact pad 34b with the palate, or a model thereof. The polymerizable material is molded to conform to the shape of the upper central incisors, with the upper central incisal edges flush against the floor of the tooth engaging box. Finger pressure can be used to assure that the polymerizable material is fully conformed to the shape of the fitted teeth. When the appliance 10 has a hole 30, during this molding process, finger pressure can be applied to the polymerizable material extruding through the hole 30 to retain the polymerizable material and force it to flow around the surfaces of the patient's teeth, instead of further extruding through the hole 30. Preferably, the polymerizable material is then partially cured as it sits engaged with the teeth. If the material is light curable, this may be done by exposing the material to a suitable high intensity light source. The appliance 10 is then removed from engagement with the teeth and fully cured. After curing, any excess of the polymerizable material can be sculpted away. Preferably, palate contact pads 34 are ground away so that extending portions 32 will no longer rest against the palatal soft tissue when appliance 10 is seated in the patient's mouth. This sculpting allows the appliance to be more comfortably worn by the patient. The molding process is effective to tightly but removably fit the appliance to the patient's teeth.

If the material is light curable, light curing can be done by exposing the material with the appliance 10 located in situ when engaged with the teeth to suitable high energy light source, generally for 1 to 2 minutes. The appliance 10 is then removed and further cured. Generally, the additional curing is conducted for about 4 to about 6 minutes. After curing, any excess of the polymerizable material can be sculpted away.

After this curing and sculpting, on occasion the dental worker will find that the material conforming to some of the useful fitting surfaces of the patient's teeth has been removed. The fitting can be improved by creating a polymer with paste-like consistency in the teeth-conforming area and again inserting the teeth or the teeth model to cause the polymer paste to flow out over the useful fitting surfaces.

Such a polymer paste can be self-curing (chemically) or can be curable by another method. For instance, the polymer paste can be TRIAD VLC gel or can be created by first applying Orthodontic Resin (L. D. Cork) and then adding SNAP self-cure resin (a quick-setting acrylic from Parkell Biomaterials Division, Farmingdale, N.Y.) to create a paste-like consistency. In the later case, repeated applications of the two components may be needed to create sufficient polymer paste. In fitting the polymer paste to a teeth model, a release material such as vasoline can be used to assure that the polymer paste does not bond to the model.

For ease of use, appliance 10 could be made available as part of a dental kit containing all the necessary materials to fit appliance 10 to a patient's mouth, such as one or more addition segments 38 and sufficient polymerizable material to fit appliance 10 to a patient's mouth and to adhere addition segments 38 to either or both of first inclined remodeling segment 36a and second inclined remodeling segment 36b. If the polymerizable material is light curable, the dental kit could also include an opaque container or other means for protecting the polymerizable material from light.

In one preferred embodiment of the appliance, the extending portions 32 and the inclined remodeling segments 36 are manufactured from polycarbonate (such as Lexan, available from General Electric, Pittsfield, Mass.) or a polymer or other material of comparable strength, biocompatability, moldability or bondability. Alternative plastics include, for example, acrylic, including methacrylate or polyaromatic carbonate. In this embodiment, the extending portions and the remodeling segments are preferably from about 4 to about 8 mm in width, more preferably from about 4 to about 6 mm in width. The appliance is preferably manufactured by injection molding.

In the measuring device 60 of the invention, illustrated in FIG. 5, the measuring rod 51 is moveable orthogonally with respect to the platform 52. One means for this moveable engagement might be a hole 53 in the platform in which the rod 51 is slidably engaged. Other means will be readily apparent to those of ordinary skill in the mechanical arts. For instance, the rod 51 can include screw grooves that engage a thumbscrew device attached to the platform 52, or the rod 51 may simply have a friction fit with platform 52. Through this means, the rod 51 can be slowly moved upwards or downwards by turning the thumbscrew. Alternatively, the hole 53 may have screw grooves that engage (i.e., mesh with) the screw ridges on the rod 51. One end of the rod 51 can have a handle portion 54 adapted to be engaged by a dental worker's fingers. When the dental worker moves the handle portion, the screw engagement or friction fit or like mechanism causes the rod 51 to move towards the palate (to measure palatal depth) or in the opposite direction (to prepare the device 60 for re-use). The rod 51 preferably has markings to measure palatal depth.

The platform 52 can have a central platform 55 and, at both teeth engaging ends, slidably engaged width measuring segments 56. These segments 56 slidably engage the platform 52 to widen or narrow the platform 52 to match the width of a patient's palate. The width measuring segments 56 can have distance markers and a means 57 for aligning the outer portions of the extensions 56 with the patient's teeth. For instance, the width measuring segments 56 can have terminal folds for engaging the outer surface of the teeth. Thus, when the width measuring segments 56 are engaged the two distances from the alignment means 57 to the central platform 55 (for both sides of the mouth) can be measured. The total of the two distances and the central platform width equals a measure of the mouth's width. This width and the palatal depth will change as a patient uses the orthodontic appliance of the invention. The measuring device 60 is preferably constructed of a sterilizable material, preferably a plastic, particularly a clear plastic.

Figure 7:
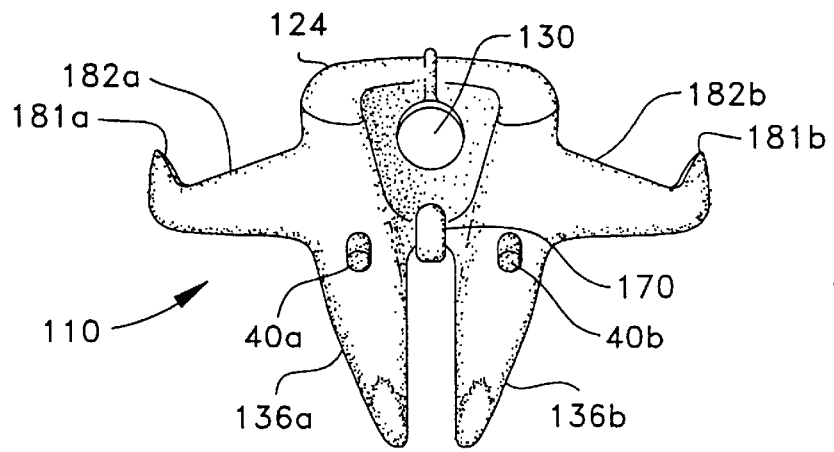
FIG. 7 shows a front view of an embodiment of the appliance that uses occlusal troughs to bond the appliance to the patients upper teeth.
Figure 8:
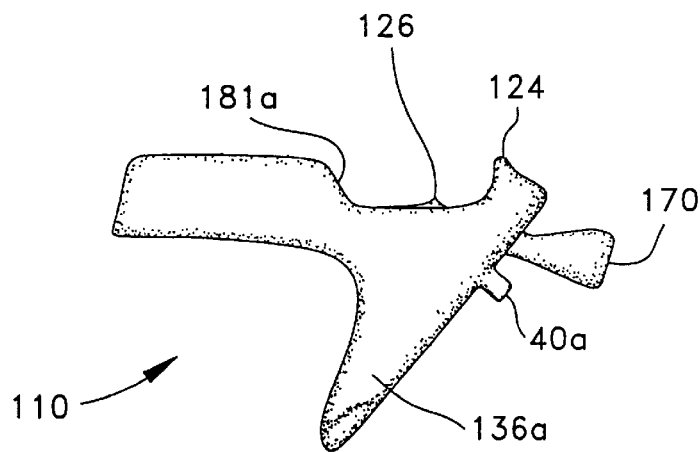
FIG. 8 shows a side view of the embodiment of the FIG. 7.
Figure 9:
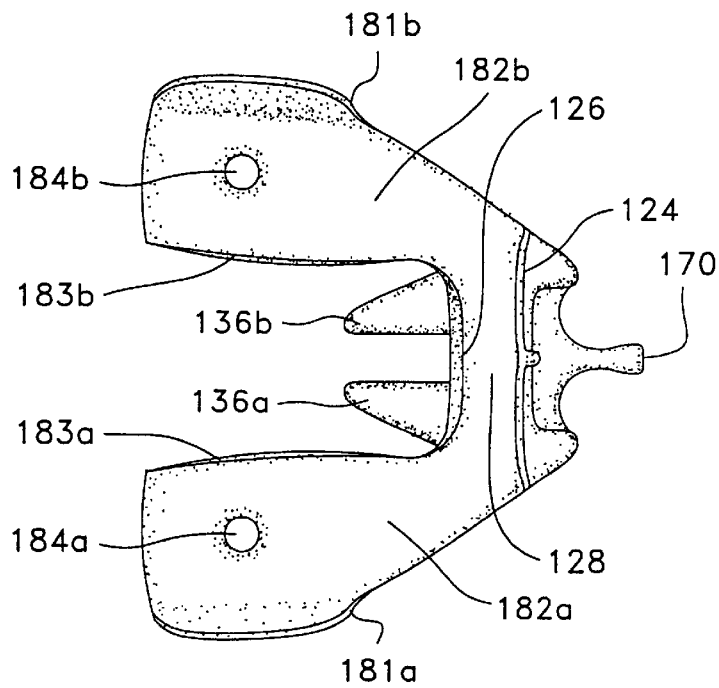
FIG. 9 shows a top view of the embodiment of the FIG. 7.

FIGS. 7, 8 and 9 show an alternative, second embodiment of the appliance of the invention. The appliance 110 has a pair of spaced inclined remodeling incline segments 136, termed first inclined remodeling segment 136a and second inclined remodeling segment 136b, that extend downward and rearward from teeth engaging box 120 (not indicated—but formed of elements 124, 126 and 128) at a predetermined angle relative to the horizontal plane of the upper jaw. The teeth engaging box 120 is formed of a front molding elevation 124, a rear molding elevation 126 and connector 128, which joins the together the front molding elevation 124 and rear molding elevation 126. The front molding elevation 124 has a hole 130. Extending from the front of appliance 110 is handle 170. Occlusal troughs 180 (not specifically shown), are formed of outer lateral molding elevations 181 (specifically first outer lateral molding elevation 181a and second outer lateral molding elevation 181b), platforms 182 (specifically first platform 182a and second platform 182b) and inner lateral molding elevations 183 (specifically first inner lateral molding elevation 183a and second inner lateral molding elevation 183b). The occlusal troughs 180 are adapted to fit under the occlusal surface of, on each side, of the upper posterior teeth. Polymerizable material can be placed in the occlusal troughs 180 and molded to the shape of the shape of the adjacent teeth. A first occlusal platform hole 184a and a second occlusal surface hole 184b help anchor the cured polymerizable material to the appliance 110. Outer lateral molding elevations 181 typically extend about 4 to about 8 mm above the floor of the occlusal trough 180 against which the posterior teeth seat. Inner lateral molding elevations 183 typically extend about 2 to about 3 mm above the floor of the occlusal trough 180 against which the posterior teeth seat. Preferred variations of this type of means for fitting an device or appliance for the mouth are described in U.S. Provisional application No. 60/000,093, filed Jun. 9, 1995, entitled "Tongue Thrust Corrective Device", attorney Docket No. 313634-102 and in the application of the same title, attorney Docket No. 313634-102A, filed concurrently herewith. These entire applications are incorporated herein by reference. It should be noted that the "palatal bridge" described in attorney Docket No. 313634-102A differs from that described herein.

First outer lateral molding elevation 181a and second outer lateral molding elevation 181b preferably fit on the outer side (i.e., the cheek side) of at least one tooth on each side of the mouth. Preferably the first outer lateral molding elevation 181a and second outer lateral molding elevation 181b each fit to the outer side of two of the posterior teeth. In a preferred embodiment, first outer lateral molding elevation 181a and second outer lateral molding elevation 181b do not block side access to the first permanent molars (i.e., the "six-year" molars). This allows use of the six-year molars to anchor other orthodontic devices, such as a band, retaining arch wires or headgear devices for correcting overjets, for instance using buccal molar tubes attached to the six-year molars.

The second embodiment appliance 110 is useful for treating children whose malocclusions interfere with good retention of the first embodiment device. The occlusal troughs of the second embodiment can be ground away once the patient's teeth and jaws have corrected sufficiently to allow good retention without the extra molding surface provided by the occlusal troughs. Thus, in a preferred embodiment, the appliance of the invention is according to the second embodiment, but also has material located so that when the occlusal troughs are ground away, the palatal stabilizing segment, which can include a palatal bridge, remains.

In treating snoring, the occlusal troughs of the second embodiment help to prevent the upper posterior teeth from elongating over time as could occur when the grinding surfaces of the posterior teeth are separated through the use of the appliance. Also in treating snoring, the location of the stop 40 is selected based on a compromise between the amount that the jaw positioning defined by the stop 40 opens the nasopharynx space and the amount of jaw repositioning the patient can comfortably accommodate.

The prefabricated appliance of the invention, in its juvenile orthodontic applications, can be supplied in a size that will fit children from about age 5 to about age 15. The prefabricated appliance of the invention, in its adult applications, can be supplied in a size that will fit almost all adults.

The appliance 10 is preferably worn at least about two to three hours a day (usually after school or after supper) and all night.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A dental appliance for fitting to the upper teeth of a patient comprising:
   a) a teeth engaging structure for engaging the upper front teeth having a cavity into which the engaged teeth fit formed by (1) a front molding elevation joined by (2) a connector to (3) a rear molding elevation;
   b) a pair of palatal extending portions bilaterally attached to rear of the teeth engaging structure and extending rearward from the teeth engaging structure;
   c) a pair of forward positioned spaced inclined remodeling segments attached to and extending from in front of, the teeth engaging structure downward and rearward at a predetermined angle designed to (1) engage the lingual surface of the lower front teeth or (2) provide a platform for an addition segment that engages the lingual surface of the lower front teeth; and
   d) raised palate contact pads supported by each of the palatal extending portions, where the palate contact pads are adapted to smoothly bilaterally contact the palate when the teeth engaging structure engages the upper front teeth and which have smooth palate contacting surfaces,
wherein the combination of the two palate contact pads and the teeth engaging structure allows three point contact with the upper mouth, thereby allowing stable positioning of the appliance within a patient's mouth.

2. The appliance of claim 1, wherein the palatal extending portions are adapted to provide, in conjunction with the teeth engaging structure and the remodeling segments, sufficient cross-sectional area of the appliance so that it cannot be swallowed.

3. The appliance of claim 2 further comprising a bridge connecting the two palatal extending portions, wherein the bridge is adapted to avoid contacting the palate and to strengthen the appliance.

4. The appliance of claim 1, wherein the teeth engaging structure comprises one or more holes located to intersect the portion of the teeth engaging structure where the tips of the front teeth of a user will be placed, wherein the holes are for engaging polymerizable material which is applied to the teeth engaging structure to fit the appliance to the shape of the patient's upper front teeth, wherein the one or more holes have beveled edges adapted to facilitate the engagement between the polymerizable material and the appliance.

5. The appliance of claim 1 further comprising a handle extending from the front molding elevation to the front of the appliance at a midline of the appliance for aligning the center of the appliance with the center of a patient's mouth or face wherein the handle is adapted to be cut away after the appliance is fitted to a patient's mouth.

6. A dental kit comprising the appliance of claim 1 and sufficient polymerizable material to fit the appliance to a patient's mouth.

7. A dental kit comprising the appliance of claim 1 and sufficient polymerizable material to fit the appliance to a patient's mouth.

8. The method of fitting the appliance of claim 7 further comprising the step of partially curing the polymerizable material in situ following the molding step and prior to the removing step.

9. A method of fitting the appliance of claim 1 to a patient comprising the steps of:
   i) fitting a polymerizable material into the cavity of the teeth engaging structure;
   ii) seating the palate contact pads on the palate;
   iii) aligning a marked center of the appliance with the centerline of the patient's face;
   iv) impressing the shape of the patient's upper front teeth into the polymerizable material into the while aligning the center of the appliance with the centerline of the patient's face;
   v) removing the appliance from the molded teeth; and
   vi) curing the polymerizable material to increase its strength.

10. A dental appliance for fitting to the upper teeth of a patient comprising:
    a) a teeth engaging structure for engaging the upper front teeth having a cavity into which the engaged teeth fit formed by (1) a front molding elevation joined by (2) a connector to (3) a rear molding elevation;
    b) a pair of palatal extending portions attached to the rear of the teeth engaging structure and which extend rearward from the teeth engaging structure;
    c) a palatal bridge joining the two palatal extending portions, wherein the palatal bridge is adapted to avoid contacting the palate and to strengthen the appliance; and
    d) a pair of forward positioned spaced inclined remodeling segments attached to the teeth engaging structure, and extending from in front of the teeth engaging structure downward and rearward at a predetermined angle designed to (1) engage the lingual surface of the lower front teeth or (2) provide a platform for an addition segment that engages the lingual surface of the lower front teeth.

11. A method of fitting the appliance of claim 10 to a patient comprising the steps of:
    i) fitting a polymerizable material into the cavity of the teeth engaging structure;
    ii) molding the polymerizable material to the shape of the patient's upper front teeth while aligning the center of the appliance with the centerline of the patient's face;

iii) removing the appliance from the molded teeth, and iv) curing the polymerizable material to increase its strength.

12. A method of fitting an appliance for correcting malocclusions in a patient, which appliance comprises a) a teeth engaging structure for engaging the upper front teeth having a cavity into which the engaged teeth fit, b) at least two palate contact pads attached to the teeth engaging structure which are adapted to smoothly bilaterally contact the palate when the teeth engaging structure engages the upper front teeth and which have smooth palate contacting surfaces, and c) a pair of forward positioned spaced inclined remodeling segments extending from in front of the teeth engaging structure downward and rearward at a predetermined angle, the method comprising the steps of:

1) fitting a polymerizable material into the cavity of the teeth engaging structure;

2) molding the polymerizable material to the shape of the patient's upper front teeth while aligning the center of the appliance with the centerline of the patient's teeth or mouth and stabilizing the seating of the appliance in the patient's mouth by contacting the palate contacting pads with the palate;

3) removing the appliance from the molded teeth;

4) curing the polymerizable material to increase its strength; and 5) after the curing, the step of sculpting the contact pads so that they will no longer rest against the palate when the appliance is seated in the patient's mouth.

13. A method of fitting an appliance to a patient, the method comprising the steps of:

a) providing a dental appliance for fitting to the upper teeth of a patient, the apparatus comprising:

i) a teeth engaging structure for engaging the upper front teeth having a cavity into which the engaged teeth fit formed by (1) a front molding elevation joined by (2) a connector to (3) a rear molding elevation;

ii) a pair of occlusal troughs attached to, and extending rearwardly from the teeth engaging structure and adapted to fit under at least one, on each side, of the upper posterior teeth; and iii) a pair of forward positioned spaced inclined remodeling segments attached to the teeth engaging structure and extending downward and rearward at a predetermined angle designed to (1) engage the lingual surface of the lower front teeth or (2) provide a platform for an addition segment that engages the lingual surface of the lower front teeth, wherein the occlusal troughs and the teeth engaging structure define a slot that allows a patient's tongue access to the palate behind the upper front teeth;

a) fitting a polymerizable material into the cavity of the teeth engaging structure and into the occlusal troughs;

c) molding the polymerizable material to the shape of the patient's upper front teeth and upper posterior teeth while aligning the center of the appliance with the centerline of the patient's face;

d) removing the appliance from the molded teeth;

e) curing the polymerizable material to increase its strength; and f) grinding away the occlusal troughs.

14. The method of claim 13, wherein the grinding step leaves sufficient material to define two palatal extending portions adapted to extend rearward along the surface of the palate and, in conjunction with the teeth engaging structure and the remodeling segments, provide for a sufficient cross-sectional area of the appliance so that it cannot be swallowed.

* * * * *